United States Patent
Finmans et al.

(10) Patent No.: US 6,887,398 B1
(45) Date of Patent: May 3, 2005

(54) ALUMINUM ACETOACETATE COMPOUNDS, THE PRODUCTION AND USE THEREOF AS PRINTING INK ADDITIVES

(75) Inventors: Peter Finmans, Duisburg (DE); Christina Diblitz, Schenefeld (DE)

(73) Assignee: RWE-DEA Aktiengesellschaft fur Mineraloel und Chemie, Hamburg (DE)

( * ) Notice: Subject to any disclaimer, the term of this patent is extended or adjusted under 35 U.S.C. 154(b) by 0 days.

(21) Appl. No.: 09/509,400

(22) PCT Filed: Sep. 25, 1998

(86) PCT No.: PCT/DE98/02860

§ 371 (c)(1),
(2), (4) Date: Jun. 19, 2000

(87) PCT Pub. No.: WO99/16739

PCT Pub. Date: Apr. 8, 1999

(30) Foreign Application Priority Data

Sep. 27, 1997 (DE) .......................... 197 42 828

(51) Int. Cl.⁷ ................................. C09K 3/00
(52) U.S. Cl. ................. 252/182.14; 106/310; 556/27
(58) Field of Search .................. 252/182.14; 106/264, 106/310

(56) References Cited

U.S. PATENT DOCUMENTS

| | | | | |
|---|---|---|---|---|
| 2,044,968 A | * | 6/1936 | Bruson | 534/13 |
| 2,871,135 A | * | 1/1959 | Weiss | 106/252 |
| 4,221,593 A | | 9/1980 | Kubo | |
| 4,264,370 A | * | 4/1981 | Turner | |
| 4,329,269 A | | 5/1982 | Takashina et al. | |
| 4,439,557 A | * | 3/1984 | Kawamura et al. | 523/216 |
| 4,976,785 A | * | 12/1990 | Nakano et al. | 525/523 |
| 5,780,525 A | * | 7/1998 | Ryang et al. | 522/81 |
| 6,051,741 A | * | 4/2000 | Etzrodt et al. | |
| 6,224,979 B1 | * | 5/2001 | Ryang et al. | 428/389 |

FOREIGN PATENT DOCUMENTS

| | | | |
|---|---|---|---|
| DE | 269142 | | 6/1989 |
| GB | 772144 | * | 4/1957 |

* cited by examiner

Primary Examiner—Matthew A. Thexton
(74) Attorney, Agent, or Firm—C. James Bushman; Browning Bushman P.C.

(57) ABSTRACT

Compositions containing aluminum trisalkylacetoacetate compounds and glycol ether and to a method for the production and use thereof, particularly as printing ink additives.

18 Claims, No Drawings

ALUMINUM ACETOACETATE COMPOUNDS, THE PRODUCTION AND USE THEREOF AS PRINTING INK ADDITIVES

BACKGROUND OF THE INVENTION

1. Field of the Invention

The invention in question is concerned with compositions containing aluminium alkyl aceto acetate compounds, their manufacture and use as additives to printing inks.

2. Description of the Prior Art

The use of aluminium tris-acetyl acetonate and aluminium tris-ethyl aceto acetate as a component in acrylate adhesives, silicone resins, intaglio inks and similar is known. For example, U.S. Pat. No. 4,221,593 discloses the use of aluminium di-isopropoxide monoethyl aceto acetate and aluminium tris-ethyl aceto acetate as gelling agents for paint binders. Depending on the reaction conditions aluminium tris-acetyl acetonate and aluminium tris-ethyl aceto acetate act as cross-linking agent of the material in question. Systems treated in this way have advantages in application. They have improved rheology, higher resistance against environmental and temperature influences or increased strength (hardness, adhesion properties). Aluminium tris-acetyl acetonate has disadvantages with regard to the toxicity, high costs of raw materials, complicated synthesis, the solid aggregate state and the low solubility in all customary solvents. Aluminium tris-ethyl aceto acetate also has low solubility in all customary solvents and a high tendency to precipitation of solid matter as a result of crystallisation phenomena.

U.S. Pat. No. 4,264,370 and GB-A-772 144 disclose mixtures containing glycol compounds, e.g., polyalkyl glycols, and aluminium compounds, with the aluminium compounds being manufactured by conversion of aluminium alcoholates with substochiometric amounts of -keto-carboxylates. The aluminium compounds according to U.S. Pat. No. 4,264,370 and GB-A-771 144 always contain at least one alkoxylate group.

The task of the invention in question is to develop aluminium compounds which do not have any or at least most of the disadvantages described above. In particular, the compounds have to be suitable as additives for printing inks and correspondingly to have a high compatibility with printing ink binders, in particular for offset printing.

SUMMARY OF THE INVENTION

Surprisingly, it was found that aluminium compounds in certain solvents are suitable for this purpose. In the compositions according to the invention in question, aluminium compounds with at least one and at the most three, preferably three, ligands of the following kind are contained:

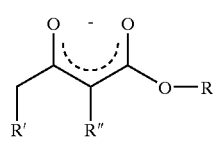

(I)

wherein

R stands for a $C_1$ to $C_{12}$, preferably a $C_1$ to $C_4$ hydrocarbon residue particularly a $C_1$ to $C_2$ alkyl residue, which may comprise 1 to 4, preferably 1 to 2, ether linkages and/or one hydroxy group, and R' and R", independent of one another, stand for H and/or one $C_1$ to $C_4$ alkyl residue, preferably for H and/or one $C_1$ to $C_2$ alkyl residue.

Glycol-ether compounds are used as further components in the composition.

DESCRIPTION OF THE PREFERRED EMBODIMENTS

Further, the aluminium compound can be a product of the above mentioned aluminium compounds (A) with compounds containing carboxyl (including acyl), ester, alcoholate or hydroxy groups, with the products being aluminium compounds which further have at least one of the above mentioned ligands (I).

Aluminium tris(methyl-aceto acetate) II (=aluminium complex of 3-oxo-butane acid methyl ester [97494-08-1]), aluminium tris (ethyl aceto acetate) III [15306-17-9]

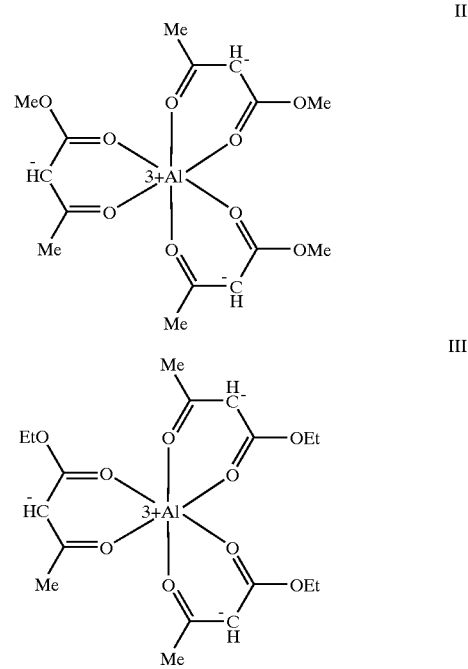

aluminium tris (2-hydroxy ethoxy ethyl aceto acetate), aluminium tris(dodecyl aceto acetate) and aluminium tris (benzyl aceto acetate) are particularly suitable aluminium compounds.

These aluminium compounds are accessible, for example, by means of derivatisation of aluminium alcoholates, preferably aluminium tri-isopropoxide by means of a ligand exchange reaction. For this, aluminium tri-isopropoxide is converted, for example with an aceto-acetic acid ester compound.

One of the problems for the use of these aluminium compounds, in particular in the printing ink industry, is the selection of a suitable solvent. Mineral oils can be used here, although they have the disadvantage that the solubility of the aluminium compounds is limited and therefore only low contents of Al can be achieved. Suitable concentrations are under 4% by weight. The mineral oils frequently used in the printing ink industry with a boiling range from 240 to 310° C. do not lead to liquid products in many cases.

In addition, when selecting the solvent, attention must be paid to the fact that processing temperatures up to 200° C. are achieved in some processes in the printing ink industry.

The addition of low-boiling solvents such as low alcohols or an excess of aceto-acetic acid ethyl ester (ethyl aceto-acetate), which is contained as a further raw material component in the additive for this event, is thus ruled out.

It was surprisingly found that glycol-ether compounds are particularly suited as solvents for the above mentioned aluminium compounds. Glycol ether compounds within the meaning of the invention in question are oligomeric compounds which essentially have n-(—X—O—)— units, wherein X may be different for each n and stands for a saturated $C_1$ to $C_6$, preferably $C_2$ to $C_4$, substituted or unsubstituted hydrocarbon, which can be connected to (one or more) arbitrary carbon atom(s) and, optionally, can for example bear one or more further —O— connections (e.g. as =O, —OH or —OR''' group). n stands for an integer from 1 to 10, preferably from 2 to 8, particularly preferably 2 to 4. The glycol ether compounds preferably have exclusively carbon, hydrogen and oxygen atoms, but can, if need be, also have a further, different atom per molecule, for example.

The end groups of the glycol ether compounds (also the side chains) can be —H, —R''', —OH or —OR''' groups. R''' preferably stands for a $C_1$ to $C_{18}$ or $C_1$ to $C_6$, particularly preferably $C_2$ to $C_4$, hydrocarbon group, preferably an alkyl group, or for a glycol ether compound with 1 to 18 carbon atoms. Preferably, the endgroup are —OR''' and —H, relative to one molecule.

Further, the glycol ether compound can, if need be, also contain a C=O connection (per molecule), e.g. in the form of an ester connection (e.g. as —COOR''' or —OOCR''').

The glycol ether compounds can, for example, also be alkylated or ethoxylated sugar molecules. Preferably, the glycol ether compound has a molecular weight of 60 to 600, particularly preferably 120 to 400 g/mol.

It is in particular preferred that the molecule comprise at least one free —OH group. Diethylene glycol-mono-n-butyl ether (DENB) and, in particular, dipropylene glycolmono-n-butyl ether (DPNB), which has a higher boiling point, are particularly preferred.

Beneficially, the aluminium compound (A) is contained with at least 50% by weight, particularly preferably 75% by weight, in the composition according to the invention relative to the sums of the components (A) and (B). Further, the aluminium compound (A) is preferably used in such a concentration that an aluminium content of the composition of at least 3% by weight results. The glycol ether connection (B) is beneficially contained in the composition with at least 5% by weight, particularly preferably at least 10% by weight, relative in each case to the sum of the components (A) and (B).

It has been proven to be particularly beneficial if the solvent is present at the start of the synthesis, for example before the addition of the alkyl aceto-acetate derivative, or is added shortly after the addition of the alkyl aceto-acetate derivative. A further beneficial measure has proven to be having the reaction at temperatures above 140° C., better above 160° C. and in particular above 190° C. Over and above these parameters, a minimum synthesis time of 5 h (e.g. above 190° C.) is preferably to be maintained. In this period, a series of reesterfication and decomposition reactions take place, apparently preventing a crystallisation of the product through the complexity of the mixture resulting. The cleaning of the products can be done by filtration, if need be after the addition of filtration agents on the basis of silicatic products or activated carbon.

Products obtained in this way are storage stable in the presence of glass, metal or plastics or under other factors caused, for example, by environmental or temperature influences.

In particular, the compositions according to the invention do not react to pollutions such as dirt, water, rust (corrosion in the interior of the uncoated container) by forming crystals, not even if the container has been opened and is then left open. In this, it is not so much the hydrolysis reaction with the air humidity (a reaction of the outer surfaces of the product with water only leads to a relatively slight acceleration of the crystallisation process) as the dust particles contained in the air which are considered to be the triggers for the crystallisation process.

The products obtained in this way have what is the unique and surprising property for Al-alcoholate derivatives of having a storage period in air of more than 6 months without opacity of the product being seen as a result of hydrolysis products or product crystals. The product is also flow-capable after this storage and has an Al content which has only inconsiderable deviations from the state at the beginning of the storage.

To sum up, the product according to the invention has the following properties:
  unique stability against hydrolysis
  fluid aggregate state despite unusually low concentration of solvents
  extraordinary properties both relative to usability for UV/EB curing of printing ink binders as well as for offset binders on the basis of alkyd resins, hydrocarbon resins and/or modified colophon resins.

The rheology of printing ink binders is normally achieved by the composition according to the invention in question by an interaction, e.g. in the form of a connection/interlinking of COOH— or OH-functional groups with the aluminium compound. If the offer of such functional groups is large, a few AL centres (0.5 to 2, preferably about 1 Al atom per sum of COOH groups and —OH groups with acid numbers of up to about 10 mg KOH/g) are sufficient. If the acid number (and the OH number) of the resin to be thickened is lower than 10 mg MOH/g, a higher concentration of the derivative containing aluminium must be available in order to achieve the same effect (1 to 15 Al atoms per sum of —COOH—+—OH— groups) in order to increase the balance, i.e. the probability of an interaction between AL—O— and COOH— or OH— groups.

Correspondingly, it is observed that the concentration of the aluminium compounds according to the invention in question used should, in printing ink binders low on COOH— and OH—, as frequently used in UV/EB curing systems on the basis of acrylic acid esters, beneficially be a factor of 5 to 15 higher than is customary in classical binders with involvement of alkyd and colophon-modified phenol resins.

In conventional binders such as alkyd resins, hydrocarbon resins and colophonmodified phenol resins, concentrations of preferably 0.3 to 2% by weight of the composition are used as an additive in the binder, particularly preferably 0.5% to 1.5% by weight (corresponding to roughly 0.03 to 0.1% by weight of aluminium in the binder). In UV/EB curing of printing ink binders, higher concentrations of additives of preferably 1 to 10% by weight of additive in the binder (corresponding to about an aluminium content of 0.06 to 0.6% by weight Al) are used, in order to build up cross-linked structures.

As printing ink binders cured by UV/EB only have a limited temperature resistance on the basis of their reactive double bonds (if the thermal limits are exceeded, there is a threat of premature hardening by polymerisation), the process of rheological modification at lower temperatures than in classical binders is to be carried out on the basis of alkyd resins and colophon-modified phenol resins. This results in lowreactive, relatively hydrolysis-stable Al-alcoholate derivatives not leading to a sufficient reaction speed.

In this context, it is surprising that the application of the aluminium alkyl acetoacetate compositions according to the invention in question in a polyester or acrylic acid ester based binder with acid and OH numbers<2 mgKOH/g leads to the most effective results with regard to the necessary Al concentration and the rheological properties of the binder.

Although the aluminium alkyl aceto-acetate compositions according to the invention in question possess a low reactivity, a much higher effectivity is achieved in relation to the Al content in this additive in the system examined than in all other state-of-the-art Al alcoholates or their derivatives.

The printing inks with additives according to the invention in question further contain colour-giving additives such as carbon black, inorganic pigments, organic pigments and/or soluble organic dyes. According to the invention, the printing inks with the additives are mainly used in offset printing. Such printing inks further contain polyester or poly-acrylic acid ester compounds as binders, preferably containing suitable groups such as reactive double bonds for cross-linking by heat, electromagnetic radiation, in particular UV radiation, or electron rays. Alongside this, initiators for the corresponding cross-linking reaction must be contained in the printing inks. Printing inks equipped in this way guarantee drying in a matter of seconds.

The compositions according to the invention in question are further suited for rheological modification of physically dry printing inks on the basis of alkyd resins, modified colophon resins or hydrocarbon resins.

EXAMPLES

Example 1

119.2 g of aluminium tri-isopropoxide (AIP) were mixed with 42.7 g of diethylene glycol-mono-n-butyl ether (DEnB) and heated to 130 to 140° C. 227.8 ethyl acetoacetate (EAA) were added at sump temperatures up to 180° C. in such a way that a distillative removal of 2-propanol (IPA) from the reaction mixture was achieved in parallel. The filtration resulted in a yellow-orange coloured clear product which formed crystals in storage in the air after about 4 days following addition of an inoculation crystal.

Example 2

419 g of AIP were presented at 100° C. and mixed with dipropylene glycol-mono-n-butyl ether (DPnB). After heating to 130° C., EAA was added within 90 min. At the same time, IPA was removed distillatively. After the completion of the addition, distillation was carried out until the head temperature dropped. The sump temperature reached a maximum of 170° C. The subsequent filtration resulted in a clear, yellow product which formed crystals in the presence of inoculation crystals in storage in the air within 4 weeks.

Example 3

1 mol aluminium-sec.butoxide (ASB) was heated to about 140° C. and mixed with a mixture of 3 mol of methyl aceto acetate (MM) and 80 g of DEnB. IPA was removed via the head. After this, the sump temperature was increased to 180° C. with further distillation. After the target temperature had been reached, there was cooling and obtaining of a yellow-orange coloured product by filtration. In the presence of inoculation crystals and with storage in the air, the formation of a solid matter was observed after about 4 h.

Example 4

3 mol of AIP were mixed with 220 g of DPnB and heated to 190° C. 9 mol of EAA were added over a period of 5 h at this temperature and IPA simultaneously removed from the reaction mixture by distillation. After cooling and filtration, an orange-coloured, clear product with an Al concentration of 5.7% by weight was obtained, which could be stored in the air for 6 months in the presence of inoculation crystals without separation of solid matters being observed.

Example 5

947 g of AIP were brought to a reaction with 1810 g of EAA within 1.5 h in such a way that distillate resulting was drawn off. After addition, the sump temperature was raised to 180° C., a vacuum applied to remove low-boilers and cooling to filtration temperature carried out. The filtration resulted in a product which can be dissolved in IPA. The Al concentration achievable in this in a storage-stable solution amounted to a maximum of 1% by weight.

Example 6

Example 6 was carried out in the same way as Example 5, albeit with a final solution in a mineral oil section typical for printing inks in the boiling range of 260 to 290° C. instead of IPA. Al concentrations about 3% by weight led to products which formed crystals within 24 h at room temperature.

Example 7

Example 7 was carried out in the same way as Example 1, albeit with the addition of DPnB after the reaction of AIP with EAA. The product obtained crystallised within a few hours after filtration and cooling.

Example 8

A standard heat-set varnish on the basis of a phenol-modified colophon resin (3 parts) and an isophthalic acid based alkyd resin (2 parts) and a mineral oil with a boiling range of 260 to 290° C. (3 parts) were mixed with 0.6 to 2.5% by weight of the product from Example 4 at a temperature of 180° C. in intensive agitation, left at this temperature for 15–60 minutes and then cooled. The resin mixture had an acid figure of about 10 and an OH figure of about 30. The additive turned the varnish with a Newton's flow property into a homogeneous and viscous-structured binder with flow limit. The exact rheological properties were achieved by slight variation of the concentration of additive in the required way.

Example 9

A UV/EB hardenable acrylate resin (acid figure<2 mgKOH/g, OH figure<2 mgKOH/g, Newton's rheology) was heated to a temperature of 10° C. in the presence of 1–5% by weight of the product obtained in Example 4. The result was a binder for printing ink marked by a strong viscosity of structure, the rheology of which could be adapted to the requirements by corresponding adjustment of the Al content.

What is claimed is:

1. A composition comprising:

(A) one or more aluminium compounds with three ligands per aluminium atom of the following kind:

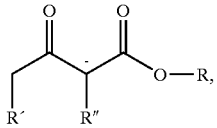
(I)

wherein:
R is a $C_1$- to $C_{12}$-hydrocarbon residue, which may comprise 1 to 4 ether linkages and/or one hydroxy group, and
R' and R", independent of one another, are selected from the group consisting of H, one $C_1$- to $C_4$-hydrocarbon residue and mixtures thereof, and (B) at least one glycol ether compound of the following structure:

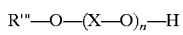

wherein:
R''' is a $C_1$- to $C_{18}$-hydrocarbon residue,
n is an integer of 1 to 10, and
X is a saturated substituted or unsubstituted $C_1$- to $C_6$-hydrocarbon, which may be linked at any carbon atom and may be different for each n, and
the glycol ether compound (B) is contained in the composition in at least 5% by weight, relative to the sum of the components (A) and (B) in the composition.

2. The composition according to claim 1, wherein the aluminium compound (A) is contained in the composition in at least 50% by weight, relative in each case to the sum of the components (A) and (B).

3. The composition according to any one of claim 1 or 2, wherein the aluminium compound is aluminium tris(methyl-aceto acetate) and/or aluminium tris(ethyl-aceto acetate).

4. The composition according to any one of claim 1 or 2, wherein X may be different for each n and stands for a substituted or unsubstituted saturated $C_1$ to $C_6$ hydrocarbon.

5. The composition according to claim 4, wherein the glycol ether compound is dipropylene glycol-mono-n-butyl ether and/or diethylene glycol-mono-n-butyl ether.

6. The composition according to any one of claim 1 or 2, wherein the composition additionally contains polyester or poly-acrylic acid ester compounds.

7. The composition according to any one of claim 1 or 2, wherein the compound additionally contains colour-giving additives selected from the group consisting of carbon black, inorganic pigments, organic pigments, soluble organic dyes and mixtures thereof.

8. A composition according to claim 4, wherein said substituted or unsubstituted saturated hydrocarbon contains 2 to 4 carbon atoms.

9. The composition of claim 4, wherein n is from 2 to 4.

10. The composition according to any one of claim 1 or 2, wherein aluminium compound (A) is contained in the composition in at least 75% by weight.

11. A composition comprising:

(A) one or more aluminum compounds with three ligands per aluminum atom of the following kind:

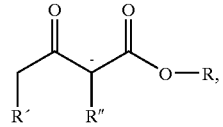
(I)

wherein:
R is a $C_1$- to $C_{12}$-hydrocarbon residue, which may comprise 1 to 4 ether linkages and/or one hydroxy group, and
R' and R", independent of one another, are selected from the group consisting of H, one $C_1$- to $C_4$-hydrocarbon residue and mixtures thereof, and (B) at least one glycol ether compound of the following structure:

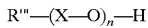

wherein:
R''' is a $C_1$- to $C_{18}$-hydrocarbon residue,
n is an integer of 2 to 8, and
X is a saturated substituted or unsubstituted $C_1$- to $C_6$-hydrocarbon, which may be linked at any carbon atom and may be different for each n, and
the glycol ether compound (B) is contained in the composition in at least 5% by weight, relative to the sum of the components (A) and (B) in the composition.

12. The composition of any one of claim 1 or 11 wherein X contains at least one oxygen linkage.

13. The composition of claim 12 wherein said oxygen linkage is selected from the group consisting of =O, —OH, —OR''' and mixtures thereof.

14. A method for the manufacture of a mixture comprising a glycol ether compound and an aluminium compound with at least one ligand per aluminium atom having the following structure:

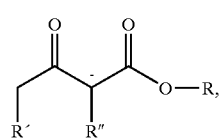
(I)

wherein R is a $C_1$ to $C_{12}$ hydrocarbon residue, which may comprise 1 to 4 ether linkages and/or one hydroxy group, R' and R", independent of one another, stand for H and/or one $C_1$ to $C_4$ hydrocarbon residue comprising reacting a $C_1$ to $C_{12}$ aluminium alcoholate with a 3-oxo-carbonic acid ester compound at a temperature of above 140° C. in the presence of a glycol ether compound.

15. The method according to claim 14, wherein the temperature is above 160° C.

16. The method according to claim 14 herein the temperature is above 140° C. for 1 to 10 hours during or after conversion.

17. The method according to claim 16 wherein the temperature is above 140° C. for 4 to 8 hours.

18. A mixture produced by any one of claims 14–17.

* * * * *

UNITED STATES PATENT AND TRADEMARK OFFICE
CERTIFICATE OF CORRECTION

PATENT NO. : 6,887,398 B1
APPLICATION NO. : 09/509400
DATED : May 3, 2005
INVENTOR(S) : Peter Finmans and Christina Diblitz Page 1 of 1

It is certified that error appears in the above-identified patent and that said Letters Patent is hereby corrected as shown below:

On Title Page, Item [73] replace Assignee "RWE-DEA Aktiengesellschaft fur Mineraloel und Chemie" with --Sasol Germany GmbH--

Signed and Sealed this

Twenty-second Day of January, 2008

JON W. DUDAS
*Director of the United States Patent and Trademark Office*